United States Patent
Peters et al.

(10) Patent No.: US 10,646,633 B2
(45) Date of Patent: May 12, 2020

(54) HEATING DEVICE

(71) Applicant: FRESENIUS MEDICAL CARE DEUTSCHLAND GMBH, Bad Homburg (DE)

(72) Inventors: Arne Peters, Bad Homburg (DE); Goekhan Oerter, Weilmuenster (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 468 days.

(21) Appl. No.: 15/510,788

(22) PCT Filed: Sep. 8, 2015

(86) PCT No.: PCT/EP2015/001811
§ 371 (c)(1),
(2) Date: Mar. 13, 2017

(87) PCT Pub. No.: WO2016/037699
PCT Pub. Date: Mar. 17, 2016

(65) Prior Publication Data
US 2017/0296728 A1    Oct. 19, 2017

(30) Foreign Application Priority Data
Sep. 12, 2014    (DE) .......... 10 2014 013 537

(51) Int. Cl.
*A61M 1/16*     (2006.01)
*H05B 3/58*     (2006.01)
(Continued)

(52) U.S. Cl.
CPC ............ *A61M 1/166* (2014.02); *A61M 1/367* (2013.01); *B01D 15/22* (2013.01); *B01D 35/18* (2013.01);
(Continued)

(58) Field of Classification Search
CPC ................. A61M 1/166; A61M 1/367; A61M 2205/3653; A61M 2209/082; A61M 5/44;
(Continued)

(56) References Cited

U.S. PATENT DOCUMENTS 2,468,390 A * 4/1949 Binz .................. B62B 1/208
                                            280/15
3,657,517 A * 4/1972 Hoyt .................. A61M 5/445
                                            219/535
(Continued)

FOREIGN PATENT DOCUMENTS

| CN | 201320207849 | 8/2013 |
| EP | 2468390 | 6/2012 |
| JP | 3028012 | 6/1996 |

*Primary Examiner* — Dana Ross
*Assistant Examiner* — Joseph W Iskra
(74) *Attorney, Agent, or Firm* — Jacobson Holman, PLLC.

(57) ABSTRACT

A heating device for one or more components of an extracorporeal circuit of a blood treatment device, in particular a dialyzer, an adsorber, or a filter, includes at least one reception region for the component, and at least one heating element for heating the component located in the receiver. The heating device has a plurality of layers, with at least one layer being a flexible layer or an elastically deformable layer.

17 Claims, 1 Drawing Sheet

(51) Int. Cl.
  *A61M 1/36* (2006.01)
  *B01D 15/22* (2006.01)
  *B01D 35/18* (2006.01)
  *A61M 5/44* (2006.01)

(52) U.S. Cl.
  CPC ............... *H05B 3/58* (2013.01); *A61M 5/44* (2013.01); *A61M 2205/3653* (2013.01); *A61M 2209/082* (2013.01); *H05B 2203/021* (2013.01)

(58) Field of Classification Search
  CPC .. B01D 15/22; B01D 35/18; H05B 2203/021; H05B 3/58
  USPC ........ 219/211, 345, 442, 528, 529, 535–537, 219/544, 549; 138/33; 165/56
  See application file for complete search history.

(56) References Cited

U.S. PATENT DOCUMENTS

| | | | | |
|---|---|---|---|---|
| 6,069,343 | A * | 5/2000 | Kolowich | ........... A61M 1/1656 219/386 |
| 2009/0299273 | A1* | 12/2009 | Lee | ........... A61M 1/28 604/29 |
| 2010/0145273 | A1* | 6/2010 | Theilacker | ........... A61M 5/44 604/114 |

* cited by examiner

HEATING DEVICE

BACKGROUND OF THE INVENTION

1. Field of the Invention

The present invention relates to a heating device for one or more components of an extracorporeal circuit of a blood treatment device, in particular of a dialyzer, a filter or an adsorber, wherein the heating device has at least one reception region for the named component as well as at least one heating element for heating the component located in the receiver.

2. Description of Related Art

During an extracorporeal blood treatment such as during a dialysis treatment, some of the blood is conducted out of the body into the extracorporeal circuit and is there subjected to a purification process, for example by dialysis.

Since an excessive cooling of the blood or of the patient has to be prevented in this process, it is known from the prior art to provide heating devices that carry out a heating of a component of the extracorporeal circuit and thus also a heating of the blood located therein.

Drum tube heaters are known from the prior art, for example, in which a plastic tube is wound multiple times around a heated drum. A disadvantage of such heating devices is a large use of space, a difficult insertion of the tube and a high material consumption.

Jacket tube heaters are furthermore known in which a plastic tube is introduced into a heated jacket, which is associated with the disadvantage of a comparatively difficult insertion.

A further heating device known from the prior art is a film heating. In this type of heating, a plastic film is coupled to a heating surface. A disadvantage in such a heating device is a difficult coupling process and a large use of space.

JP3028012 U discloses a holder for a dialyzer that comprises a heating device having a controllable temperature. The holder comprises a heatable inner surface having a temperature sensor and can be fastened to a stand by means of suitable fastening means.

Arrangements known from the prior art in some cases admittedly have good handling and good efficiency, but suffer from the disadvantage of a complex mechanical construction such as in an automatic coupling by a device. Other known embodiments admittedly have a simple mechanical construction, but a poor efficiency, difficult handling and a large use of space such as is the case with a tube drum heating. Further known embodiments such as a film construction in the heating receiver with a manual film coupling bring about the advantage of good efficiency, but have a large use of space, require difficult handling and have a mechanically complex construction.

The large use of space of known embodiments results from the fact that an additional element has to be installed in the system that heats liquid in a plastic article.

SUMMARY OF THE INVENTION

It is the underlying object of the present invention to further develop a heating device of the initially named kind such that a simple coupling of the component to be heated and an efficient heating is possible.

This object is achieved by a heating device having the features described herein. Provision is accordingly made that the heating device has a plurality of layers, with at least one layer being a flexible layer or an elastically deformable layer. It is possible by such a layer that the heating device also easily adapts to the outer surface of the component to be heated in the event of irregularities or that the coupling of the component to the heating device is facilitated because tolerances in the coupling can be compensated by the elastic or flexible layer.

The present invention preferably utilizes already present surfaces and thus combines a space-saving, efficient construction with a simple design and a simple handling. It is a substantial advantage of the invention that the heating device simultaneously represents a holder for a dialyzer, a filter or an adsorber and thus has a space-saving and cost-saving effect.

Provision is made in a preferred embodiment of the invention that the heating device has at least one elastically deformable layer and at least one flexible layer. These two layers preferably contact one another directly. In this respect, the flexible layer can form the heatable inner surface of the receiver for the component.

Provision can furthermore preferably be made that the heating device has at least one rigid layer. This rigid layer can, for example, form the outer layer of the heating device, i.e. can represent its outer side. It is, however, also conceivable that the rigid layer forms the heatable inner surface of the receiver for the component.

Provision is preferably made that the rigid layer has a Young's modulus of 700 N/mm$^2$ or more. The higher the Young's modulus, the more stable the receiver.

Provision can furthermore be made that the heating device has at least one rigid layer, at least one elastically deformable layer and at least one flexible layer.

The compressive force of the elastically deformable layer can be at 25% compression in the range from 0.01 N/mm$^2$ to 0.7 N/mm$^2$. The more elastic this layer is, the more advantageous it is for the heating device. If the geometry of the dialyzer, filter or adsorber is produced within tight tolerances, the use of hard rubber or of a material having a comparable elasticity could also be considered.

The maximum bending resistance of the flexible layer with respect to the width of the film can be at 6.57 Nmm$^2$/mm or less. The flexible layer should have a bending resistance that is as small as possible.

The elastically deformable layer can be arranged between the rigid layer and the flexible layer.

A preferred layer design comprises the outer side of the heating device being formed by the rigid layer, the elastically deformable layer adjoining it, and the inner layer, i.e. the layer in contact with the component, being formed by the flexible layer.

To ensure a sufficient deformability, provision is preferably made that the elastically deformable layer is comparatively thick and preferably has a greater thickness than the rigid layer and/or than the flexible layer.

The flexible layer can, for example comprise silicone, polyimide, carbon or aluminum, in particular an aluminum film or can comprise one or more of these components.

The elastically deformable layer can furthermore be formed from rubber or foam, in particular from silicone foam, and can comprise one or both of these components.

The rigid layer can consist of plastic, in particular PP, PET, aluminum or hard foam or can comprise one or more of these components.

The wall of the reception region, i.e. the inner surface of the heating device that is connected to the component, can be formed by the flexible layer or by the rigid layer or by the elastic layer. It is particularly advantageous if the elastic layer and/or the flexible layer forms the inner side of the receiver since then a good contact of the heating device at the component can be achieved.

Provision is made in a further embodiment of the invention that the elastic layer or the flexible layer is formed by a floating support. In this case, a rigid layer can be received in a floating support, with the rigid layer forming the receiver for the component to be heated, for example. In such an embodiment, the advantage results that tolerances in the coupling can be compensated because the receiver is not rigidly fixed to the treatment device, in particular to a dialysis machine, but rather has a certain movability.

The present invention does not only relate to the heating device per se, but also to a combination of the heating device and a component of an extracorporeal circuit that is arranged in its reception region and which can in particular be a dialyzer, a filter or a tube.

To ensure a good contact of the component at the heated inner surface of the heating device, provision can be made that the outer dimension such as in particular the outer diameter of the component corresponds to the inner dimension of the receiver or exceeds it before the component is placed into the reception region.

The heating element can, for example, be arranged between two of the named layers or in at least one layer of the heating device. It is, for example, conceivable that the flexible layer is the heating element. The heating element can thus, for example, be formed as a silicone heating element.

The present invention furthermore relates to a blood treatment device, in particular to a dialysis machine having at least one heating device in accordance with the invention.

The heating device preferably has a concave receiver.

The heating device generally preferably serves as a holder element for the component to be heated.

It surrounds the component to be heated over its full surface or over a part region of the periphery such as over a region of approximately 150° or also more. An area utilization of >50% preferably takes place, i.e. more than half the heatable surface of the component is preferably heated. The heating device is preferably thermally insulated toward the rear side, i.e. at the side remote from the receiver.

It is conceivable that the heating device comprises a plurality of parts that can be opened to insert the component and can then be closed. The closing can then take place such that the component is pressed into the receiver.

The component that is arranged in the receiver or is located therein can, for example, be a component having a rigid or flexible outer surface such as a dialyzer, an adsorber, a filter such as a sterile filter, a microfilter or a tube, etc.

BRIEF DESCRIPTION OF THE DRAWINGS

Further details and advantages of the invention will be explained in more detail with reference to an embodiment described in the drawing. There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
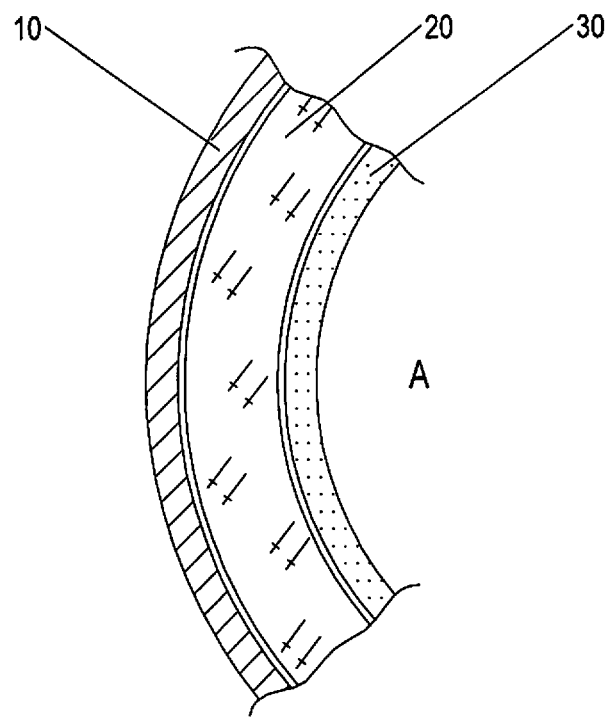
FIG. 1: a sectional view through a heating device in accordance with the invention.

FIG. 1 shows by the reference numeral 10 the outer side or rear side of the heating device in accordance with the invention that is remote from the reception region A and that, for example, comprises a plate such as a metal plate or plastic in a shape of shell geometry.

The reception region A preferably serves the reception of a disposable of a blood treatment device to be heated such as a filter or a dialyzer or an adsorber.

An elastically deformable layer 20 that e.g. comprises a silicone foam adjoins this rigid layer 10. The layer 20 can, for example, have a thickness in the range between 5 mm and 15 mm and can preferably have a thickness of 10 mm.

This layer is followed by a flexible inwardly disposed layer 30 that forms the heating element and the heated inner side of the heating device. The flexible layer 30, for example, comprises silicone having integrated heating wires or a heatable carbon film and has a smaller thermal resistance than the elastic layer 20.

In addition, further flexible layers can be present for electrical insulation or mechanical surface strength.

As can be seen from FIG. 1, the layers 10, 20, 30 are concentrically arranged with respect to one another in the detail shown, i.e. at the level of the reception region A.

It can furthermore be seen from FIG. 1 that the thickness of the elastic layer 20 is larger than the thickness of the layer 10 and than the thickness of the layer 30.

The rigid housing 10 establishes the mechanical stability of the heating device and presses the flexible element 30 indirectly via the elastically deformable component 20 toward the component located in the reception region A, such as toward a dialyzer. It is achieved by the elastic layer 20, on the one hand, and by the flexible layer 30, on the other hand, that the heating element—in the form of the flexible layer 30—can adapt easily to the surface and to any irregularities located thereon such that a particularly efficient heat transfer from the heating device to the component and thus ultimately a particularly efficient heating of the blood flowing in the component can take place.

Figure 2:
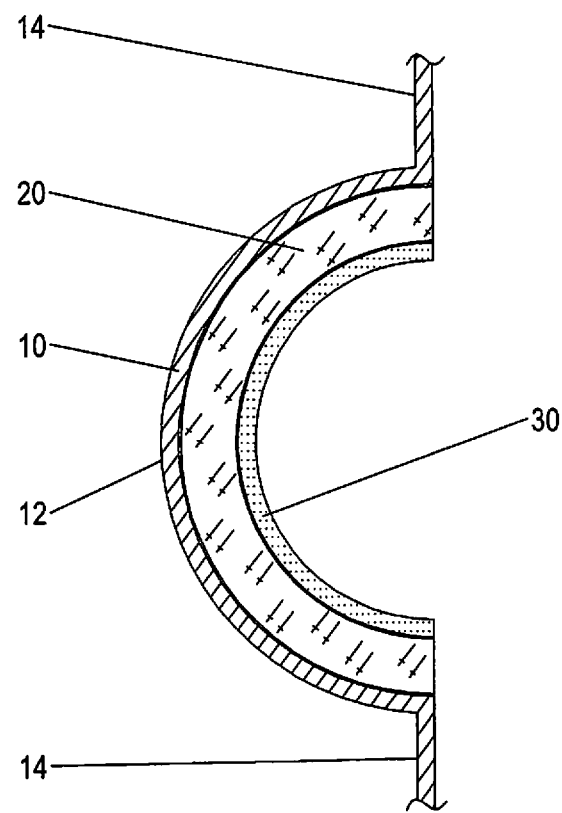
FIG. 2: a further sectional view through a heating device in accordance with the invention.

FIG. 2 shows the total heating device of which a detail is shown in the region of the reception region A in FIG. 1.

Reference numeral 10 characterizes the housing that has a concave section 12 in which the deformable layer 20 and the flexible layer 30 are located. The concave section is adjoined at the top and at the bottom by straight sections 14 that are formed without the layers 20, 30 and that, for example, form fastening sections by means of which the heating device can e.g. be fastened to a dialysis machine.

In the embodiment shown in the Figures, the heating device represents a receiver that, for example, hold and fixes the dialyzer, nestles up to it and compensates tolerances.

The heating device in accordance with the embodiment shown comprises a flexible, flat element for coupling to the dialyzer or the like and comprises an elastic, thicker layer. The flexible, flat element, that, for example, comprises silicone or polyimide or carbon or aluminum film, has a smaller thermal resistance than the elastic, deformable thicker element that can, for example, be designed as foam, e.g. as silicone foam.

A rigid housing gives the heating device the sufficient mechanical stability. It can, for example, consist of PP or PET or also of a metal such as aluminum or of hard foam. It presses the deformable heating component, i.e. for example the flexible layer toward the component to be heated such as to the surface of a dialyzer, filter, etc.

This component can, for example, represent a plastic housing having small thermal conductivity or a housing having high thermal conductivity such as a housing composed of a thermally conductive plastic or of other materials. The housing of the component such as the filter housing or the dialyzer housing is preferably rigid.

Provision is made in a further embodiment of the invention that the heating device is made up of a rigid element that serves the coupling to the component to be heated and of an elastic element. The rigid element, that can be formed from aluminum or plastic, for example, can have a smaller thermal resistance than the elastic element that can e.g. consist of rubber or of foam.

In a further embodiment of the invention, the receiver for the component to be heated is rigid. It is floatingly supported in an elastic element or flexible element. This element can, for example, be located at the housing and in particular at the machine plate of a dialysis machine.

A good coupling, a simple insertion of the component to be heated and an efficient use of area are made possible by the present invention.

The heating device preferably has a temperature sensor and a temperature regulation unit that maintains the temperature at a specific value or in a specific range.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A heating device for a component of an extracorporeal circuit of a blood treatment device, the heating device comprising:
   a reception region for receiving the component to be heated;
   a heating element for heating the component located in the reception region;
   a flexible layer;
   an elastically deformable layer; and
   a rigid layer,
   with the layers being configured such that the rigid layer is an outer side of the heating device, the elastically deformable layer is arranged between the flexible layer and the rigid layer, and the flexible layer is an inner side that contacts the component being heated.

2. The heating device in accordance with claim 1, wherein the rigid layer has a Young's modulus of 700 $N/mm^2$ or more.

3. The heating device in accordance with claim 1, wherein a compressive force at 25% compression of the elastically deformable layer is in a range from 0.01 $N/mm^2$ to 0.7 $N/mm^2$.

4. The heating device in accordance with claim 1, wherein the flexible layer has a maximum bending resistance with respect to a width of the flexible layer of 6.75 $N/mm^2/mm$ or less.

5. The heating device in accordance with claim 1, wherein the elastically deformable layer has a thickness that is greater than a thickness of at least one of the rigid layer and the flexible layer.

6. The heating device in accordance with claim 1, wherein the flexible layer has a material of construction that includes at least one of silicone, polyimide, carbon, and aluminum.

7. The heating device in accordance with claim 1, wherein the elastically deformable layer has a material of construction that includes at least one of rubber and foam.

8. The heating device in accordance with claim 1, wherein the rigid layer has a material of construction that includes at least one of a plastic, aluminum, and a hard foam.

9. The heating device in accordance with claim 1, wherein the component received in the reception region is a dialyzer, a filter, or a tube.

10. The heating device in accordance with claim 9, wherein an outer dimension of the component corresponds to, or exceeds, an inner dimension of the reception region.

11. The heating device in accordance with claim 1, wherein the heating element is arranged between two of the the flexible layer, the elastically deformable layer, and the rigid layer, or in at least one of the flexible layer, the elastically deformable layer, and the rigid layer.

12. A blood treatment device comprising a heating device in accordance with claim 1.

13. The heating device according to claim 6, wherein the flexible layer includes an aluminum film.

14. The heating device according to claim 7, wherein the elastically deformable layer includes a silicone foam.

15. The heating device according to claim 8, wherein the plastic of the rigid layer is at least one of a PP and a PET.

16. The heating device according to claim 11, wherein the heating element is arranged in the flexible layer.

17. The blood treatment device according to claim 12, wherein the device is a dialysis machine.

* * * * *